United States Patent [19]

Scott et al.

[11] Patent Number: 4,862,060
[45] Date of Patent: Aug. 29, 1989

[54] MICROWAVE APPARATUS FOR MEASURING FLUID MIXTURES

[75] Inventors: Bentley N. Scott, Richardson; Y. Sam Yang, Plano, both of Tex.

[73] Assignee: Atlantic Richfield Company, Los Angeles, Calif.

[21] Appl. No.: 932,068

[22] Filed: Nov. 18, 1986

[51] Int. Cl.[4] .............................................. G01N 22/00
[52] U.S. Cl. ................................ 324/58.5 A; 73/61 R; 324/58.5 R
[58] Field of Search .................... 73/61.1 R, 61 R; 324/58.5 A, 58.5 B, 58.5 R, 58.5 C

[56] References Cited

U.S. PATENT DOCUMENTS

| | | | |
|---|---|---|---|
| 3,079,552 | 2/1963 | Walker | 324/58.5 A |
| 3,498,112 | 3/1970 | Howard | 73/61.1 R |
| 3,612,996 | 10/1971 | Bleackley | 324/58.5 A |
| 3,693,079 | 9/1972 | Walker | 378/53 |
| 3,965,416 | 6/1976 | Friedman | 324/58.5 B |
| 4,048,844 | 9/1977 | Dunikowski | 73/61.1 R |
| 4,206,399 | 6/1980 | Fitzky et al. | 324/58.5 C |
| 4,240,028 | 12/1980 | Davis, Jr. | 324/61 R |
| 4,257,001 | 3/1981 | Partain | 324/58.5 C |
| 4,311,957 | 1/1982 | Hewitt et al. | 324/58.5 R |
| 4,352,288 | 10/1982 | Paap et al. | 73/61 R |
| 4,361,801 | 11/1982 | Meyer et al. | 324/58.5 R |
| 4,367,440 | 1/1983 | Mazzagatti | 324/445 |
| 4,423,623 | 1/1984 | Ho et al. | 73/61 R |
| 4,429,273 | 1/1984 | Mazzagatti | 324/61 R |
| 4,499,418 | 2/1985 | Helms et al. | 324/58.5 A |
| 4,503,384 | 3/1985 | Nagy et al. | 324/58.5 R |
| 4,764,718 | 8/1988 | Revus et al. | 324/58.5 A |

Primary Examiner—A. D. Pellinen
Assistant Examiner—H. L. Williams
Attorney, Agent, or Firm—Michael E. Martin

[57] ABSTRACT

An apparatus for measuring the concentration of one material in another, such as the concentration of water in crude or refined mineral oil, comprises a conduit for receiving and discharging a continuous flow stream of the fluid mixture and which is formed as part of a coaxial microwave transmission line. A microwave or radio frequency range signal generator in the form of an unbuffered oscillator is connected to the transmission line for generating a high frequency signal which may be varied by a voltage controlled oscillator tuning circuit. A signal receiver monitors the change in frequency caused by impedance pulling of the oscillator due to the change in fluid dielectric constant and transmits a differential frequency signal to a frequency counter and microprocessor for comparison of the measured signal with known reference signals for determining the percentage of one fluid mixed in the other in the flow stream. The apparatus measurement section is adapted to provide for connecting standard microwave coaxial connectors to a relatively large diameter pipe or conduit comprising the coaxial transmission line portion of the measurement section.

17 Claims, 3 Drawing Sheets

MICROWAVE APPARATUS FOR MEASURING FLUID MIXTURES

BACKGROUND OF THE INVENTION

1. Field of the Invention

The present invention pertains to an apparatus including a high frequency, unbuffered, voltage controlled oscillator for transmitting radio frequency or so called microwave signals through a coaxial conductor or waveguide structure, which may comprise a portion of a fluid pipeline or the like, for sampling the composition of mixtures of substances as a function of the dielectric properties thereof. In particular, the concentration of small quantities of liquids such as water in liquids such as oil are measured by comparing the change in the output signal of the oscillator with signals corresponding to known concentrations or compositions of mixtures.

2. Background

Various types of apparatus have been proposed for measuring the concentration of one substance in another, particularly the concentration of a liquid or flowable substance in another liquid or flowable substance. One technique which is useful utilizes radio frequency or microwave energy measurement. Various devices which utilize the broad concept of determining composition of matter by measuring changes in a microwave signal are disclosed in U.S. Pat. Nos. 3,498,112 to D. D. Howard; 3,693,079 to C. W. E. Walker; 4,206,399 to H. G. Fitzky, et al; 4,311,957 to S. J. Hewitt et al; 4,361,801 to W. Meyer et al; 4,240,028 to L. A. Davis, Jr.; 4,352,288 to H. J. Paap et al; 4,499,418 to D. A. Helms et al; 4,367,440 and 4,429,273, both to R. P. Mazzagatti.

Although various systems utilizing microwave transmissivity or signal alteration characteristics have been proposed in the prior art, certain considerations in utilizing microwave energy to detect the presence of the concentration of one medium in another have not been met by prior art apparatus. In particular, it is desirable in certain instances to be able to accurately measure, on a continuous basis, the concentration or change in concentration of one fluid in another and particularly where the concentration of one fluid is a very low percentage of the total fluid flow rate or fluid mixture quantity. It is also desirable that the signal change caused by the presence of one substance or medium in another be easily measured and be relatively error free, again, particularly in instances where measurements of low concentrations of one substance such as a fluid in another substance such as another fluid are being taken. Moreover, it is important to be able to transmit the microwave signal through a true cross section of the composition being sampled or measured to enhance the accuracy of the measurement.

One relatively important application of microwave energy for measuring the properties of a fluid mixture is in the transportation and handling of crude or refined oils wherein it is desirable to measure the concentration of water or some other fluid in the oil. In this instance, relatively small concentrations of water or other fluids are usually found in the oil being transported after preliminary processing or separation procedures are carried out. However, in some transport systems such as in the Trans-Alaska Pipeline System, the very large quantities of oil being transported make it highly desirable to be able to make accurate measurements of the percentages of other fluids present in the oil, such as water, so that separation and treatment facilities can be adjusted to accomodate the presence of the water and tariffs for transporting the oil can be adjusted accordingly.

Therefore, it has been considered desirable to develop a microwave based system for determining the concentration of water in oil, for example, in various quantities as a percent of the total flow. It is to this end that the present invention has been developed with a view to providing an improved apparatus for determining the concentration of one medium in another, such as water or other liquids in crude or refined mineral oils.

SUMMARY OF THE INVENTION

The present invention provides an improved apparatus for utilizing a microwave energy signal which varies when transmitted through a transmission line, with the concentration or content of one medium in another which is present as a dielectric material in a coaxial transmission path or waveguide structure. In particular, the system of the present invention utilizes a coaxial transmission line or conductor wherein a fluid medium is flowing through the conductor or transmission line between an outer conductor and a center conductor such that the microwave energy is contained in a true cross section of the fluid being measured.

In accordance with one aspect of the present invention, a relatively high frequency unbuffered oscillator generates radio frequency or so-called microwave energy which is transmitted through an RF transmission line which also receives a flow stream of fluid. The net complex impedance of the transmission line varies with the concentration of one fluid in another to change the operating frequency of the oscillator which is measured and compared with a known frequency range to determine the concentration of one fluid in another from reference data. Signal amplitude data may be used to cross check range and for determination of the effects of salinity of the fluid contaminant, such as water. Salinity concentration is important to determine since it affects the frequency—amplitude relationship.

In accordance with another aspect of the invention, an apparatus is provided which includes an oscillator whose normal operating frequency is varied in accordance with impedance of the signal generated by the oscillator over a frequency range which permits the determination of very small concentrations of one fluid such as water in another fluid such as oil or vice versa, and wherein the normal or resonant operating frequency of the oscillator circuit varies over a limited range and then returns to the original frequency. The circuit of the apparatus of the present invention includes means for detecting the full range excursion of the operating frequency and for counting the number of excursions to determine the presence of higher concentrations of one medium in another within very narrow ranges of change and whereby the accuracy of determination of the exact concentration of one medium in the other is relatively great.

In accordance with still another aspect of the present invention, there is provided an apparatus particularly adapted for field application in crude oil and other hydrocarbon fluid transmission pipelines and transport systems for measuring a true cross-sectional flow stream of liquid with minimal introduction of errors in the apparatus output signal. The system includes a measuring cell configured as a coaxial transmission line which is adapted to provide microwave signal input and output sections which can accommodate conventional conductor connector devices and the like.

The system for measuring the concentration of a fluid such as water in another fluid such as oil in accordance with the present invention, is also unique in that a conventional unbuffered or unisolated oscillator circuit may be used in conjunction with a coaxial transmission line which is also a fluid conductor for measuring fluid mixtures wherein a concentration or percentage of the total mixture of one fluid or substance is relatively small as compared to the total volume of fluid or substance being conducted through the measuring section of the transmission line.

Those skilled in the art will recognize the above described advantages and superior features of the present invention as well as other aspects thereof upon reading the description which follows in conjunction with the drawing.

DESCRIPTION OF A PREFERRED EMBODIMENT

In the description which follows, like parts are marked throughout the specification and drawing with the same reference numerals respectively. The drawing figures are not necessarily to scale and certain elements are shown in schematic form in the interest of clarity and conciseness.

Figure 1:
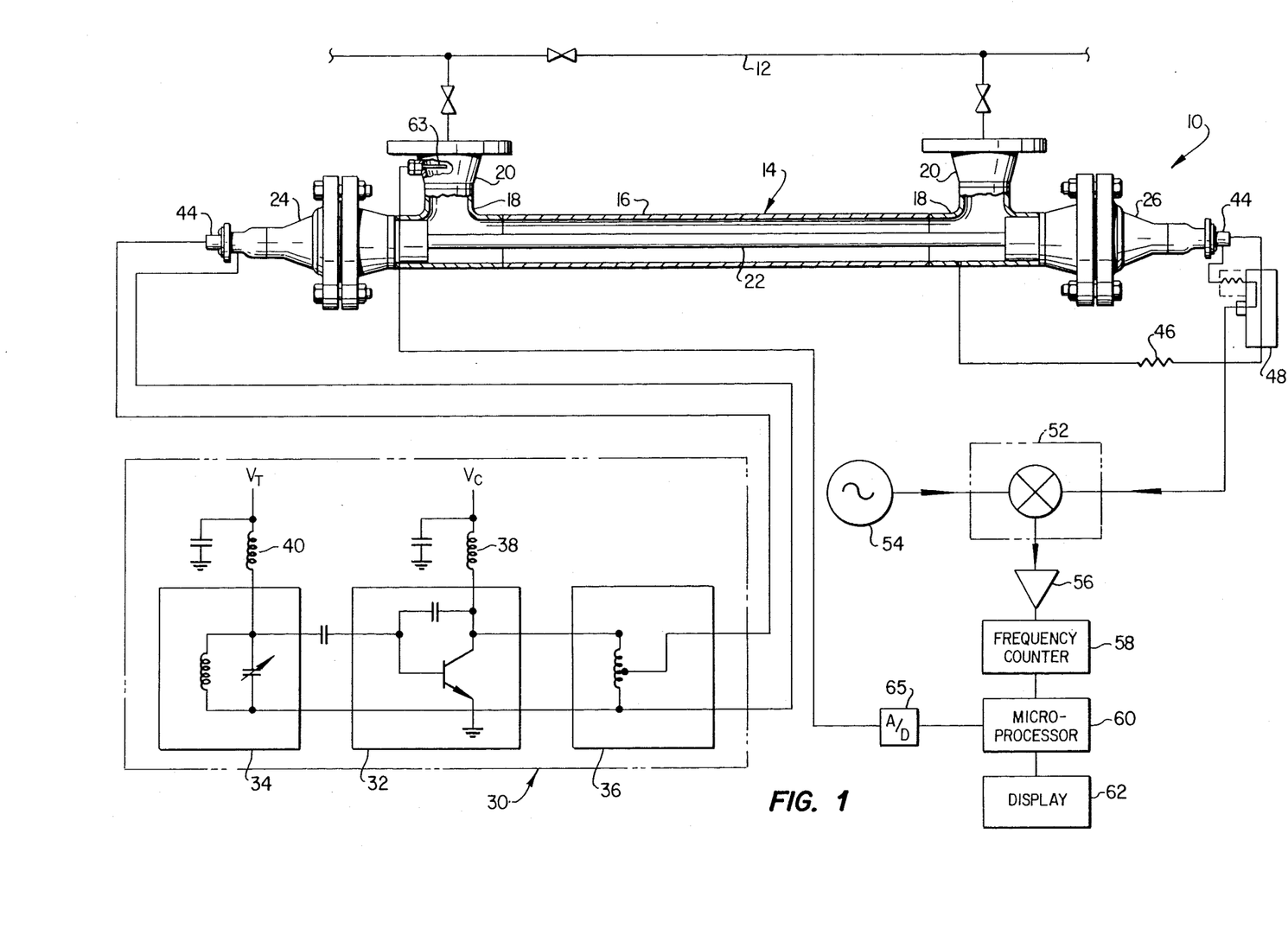
FIG. 1 is a schematic diagram of the apparatus of the present invention.

Referring to FIG. 1, an improved apparatus for measuring the concentration of a liquid in a liquid flow stream is illustrated and generally designated by the numeral 10. The apparatus 10 is particularly adapted for interconnection with a fluid transmission pipeline 12 for sampling the flow stream through the pipeline or by actually becoming interposed as a part of the pipeline. The apparatus 10 includes a fluid flow conducting and measurement section 14 comprising a conventional outer conduit section 16, spaced apart "T"sections 18, and conventional weldneck pipe flanges 20. The liquid mixture to be measured for determining the concentration of one medium in the other may be conducted through the conduit 16 on a continuous basis and the measurement section 14 may comprise part of a fluid transmission pipeline. An elongated center conductor 22 extends through the conduit 16 between opposed support end parts 24 and 26 which will be described in further detail herein in conjunction with FIG. 2. The center conductor 22 may comprise a generally cylindrical rod member or tube member and is preferably coaxially arranged in the conduit 16, including the opposed end or "T"sections 18. The measurement section 14 can be configured to contain a quantity of fluid or other compositions of matter without continuous or intermittent flow through the measurement section for use of the apparatus in laboratory sampling procedures, for example.

The apparatus measurement section 14 is operably connected to a source of radio frequency or so-called microwave energy comprising an unbuffered or unisolated oscillator, generally designated by the numeral 30. The oscillator 30 includes an active circuit 32 operably connected to a tuning circuit 34 and to an impedance matching network circuit 36. The active circuit 32 is adapted to receive a constant DC voltage, $V_c$, from a source, not shown, by way of a filter circuit 38, and the tuning circuit 34 is adapted to receive a controllable DC voltage, $V_t$, from another source, not shown, by way of a second filter circuit 40. An unbuffered oscillator such as the oscillator 30 is one which has an appreciable load pulling characteristic. The fundamental operating frequency of the oscillator is changed as the complex load is changed on the output circuit of the oscillator. Depending on the coupling factor of the output circuit the load pulling characteristic can be negligible or substantial. Increasing load pulling factor increases the possibility of so-called spectral breakup (multiple frequency operation) which would render the desired measurement of the oscillator signal impossible. The oscillator 30 may be of a type commercially available, such as from the Watkins-Johnson Company, Scotts Valley, Calif. as their Model D-827 voltage controlled oscillator. The exemplary oscillator 30 has a maximum load pulling characteristic of about 35 MHz at a nominal 1.60 GHz operating frequency into all phases of a short circuit at the end of a 50 ohm line stretcher (approximately 0.5 db return loss). If such a line was of constant loss versus phase, the frequency of the oscillator would return to its original frequency at any particular phase every 360° multiple of the reflection co-efficient at that phase.

The oscillator 30 is operably connected to the apparatus measurement section 14 through a suitable connector 44 which is in electrically conductive engagement with the center conductor 22 at the end part 24 and the oscillator 30 is also in communication with the center conductor 22 through a second connector 44, a resistance 46, and with the outer conductor, as illustrated. The end part 26 is also adapted to interconnect the center conductor 22 with a ten db directional coupler 48 which is operable to sample the energy transmitted through the coaxial measurement section 14. The coupler 48 could also be placed in circuit between the oscillator 30 and the measurement section 14. The resistor 46 could possibly be eliminated with a short circuit according to the characteristics of the oscillator. In accordance with the present invention, an oil/water mixture flowing through the conduit 16 provides a certain dielectric constant which changes the impedance characteristics of the measurement section 14 and in accordance with the percentage of water or other fluid present in the oil medium, changes the operating frequency of the oscillator 30. The oscillator signal amplitude characteristics also vary with the concentration of water or change in composition of matter being measured, although the frequency characteristic provides for more accurate measurements.

The coupler 48 is connected to a receiver system which includes a mixer 52 and an isolated oscillator 54 which is tuned to provide a differential output signal of a frequency which can be amplified by an amplifier 56 and can be counted by a frequency counter 58. The counter 58 is operably connected to a microprocessor 60, which in turn is suitably connected to a display or readout device 62. The mixer 52 may also be of a type commercially available from the Watkins-Johnson Company as their Model WJ-M7B. The amplifier 56 is also available from the abovementioned company as their Model WJ-A38. The frequency counter 58 may be of a type manufactured by Hewlett-Packard as their Model 5342A and the microprocessor 60 may also be of a type manufactured by Hewlett-Packard as their Model 9836. The receiver system described above may also be modified to include a signal amplitude detector, not shown. The system illustrated in the drawing figures preferably comprises means for compensating for the temperature of the medium being measured in the measurement section 14, including a thermocouple 63 interposed in the flow path of the medium. The thermocouple 63 is suitably connected to a conversion circuit 65 to provide a suitable digital signal to the microprocessor 60 related to the temperature of the medium being measured.

In operation, the changing dielectric constant presented by the liquid medium being pumped through the measurement section 14 as caused by the presence of varying amounts of water in oil, for example, causes the oscillator 30 to change its operating frequency over a relatively narrow frequency band as compared with the nominal operating frequency of the oscillator. The oscillator 30, in a preferred form, can be pulled from its nominal operating frequency through a range of about 20 MHz by the changing dielectric constant of the medium flowing through the measurement section 14 wherein the percentage of water in oil, for example, varies over a range of approximately two percent of the total fluid volume. The sensitivity of the oscillator 30 to the change in the water content of the oil/water mixture is particularly high due to the operating frequency of the oscillator since the phase change of the relatively high frequency signal is magnified to some extent by the decreased wavelength at these frequencies and the length of the measurement section 14 is multiple wavelengths. A corresponding increase in sensitivity of the system 10 can also be obtained by increasing the length of the measurement section 14 and keeping the frequency of the signal generated by the oscillator 30 constant.

By sweeping the oscillator operating frequency across a frequency span of approximately 400 MHz through adjustment of the resonant tuning circuit 34, a change in the operating frequency for a particular tuned frequency may be compared with the output of the oscillator 54 and a differential, relatively low frequency signal may be output from the mixer 52 to the frequency counter 58. The frequency counted by the counter 58 may be compared with frequency data stored in the microprocessor 60 and corresponding to a range of percentages of one medium in another such as water in oil. This comparison signal may then be suitably output to a display 62 to display the amount of or concentration of one medium in the other. The frequency counter 58 may include suitable analog to digital conversion devices, not shown.

The oscillator 30, after being pulled through its maximum deviation from its nominal resonant frequency at a particular tuned condition, will return to the original frequency of operation for a given range of concentration of one substance in another. Accordingly, additional measurements must be made to determine whether the system 10 is perceiving a concentration of a medium such as water in oil in the range of say zero to two percent or in a range of two percent to four percent wherein each two percent change corresponds to the full frequency range of operation of the oscillator.

Figure 3:
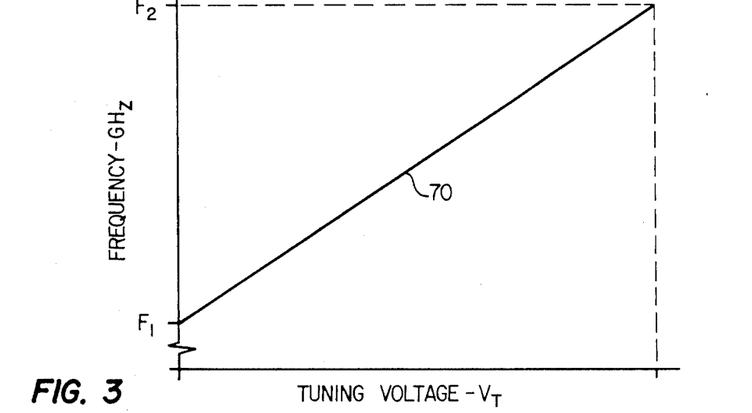
FIGS. 3 through 5 comprise diagrams showing the frequency characteristic versus the tuning circuit voltage of the unisolated oscillator for its full range of frequencies under loads corresponding to certain concentrations of one liquid such as water in another liquid such as oil.
Figure 4:
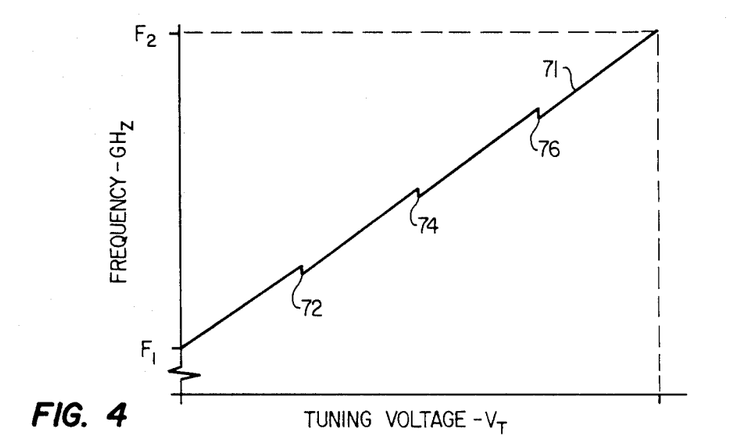
Figure 5:
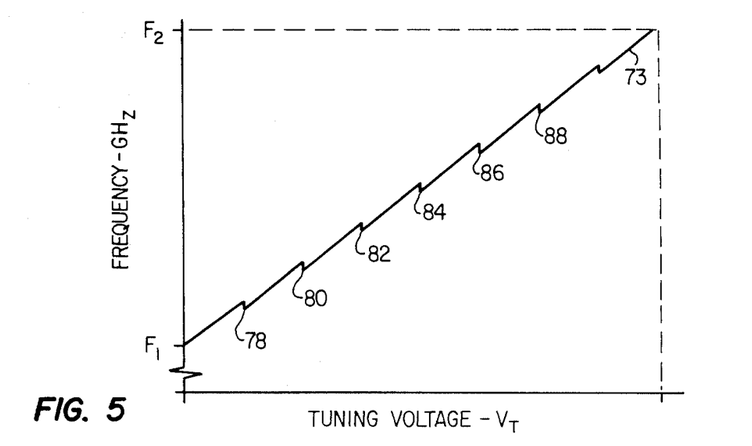

Referring now to FIG. 3, there is illustrated a diagram showing the variation in the output signal frequency of the oscillator 30 over its maximum tunable frequency range when tuned by the tuning circuit 34 when the circuit is terminated into its characteristic impedance. A voltage controlled oscillator such as the oscillator 30, when swept across its maximum range as determined by changing the tuning voltage $V_T$ will exhibit a characteristic indicated by the line 70 for a perfect or balanced load. If the dielectric constant of the composition present between the conductors 16 and 22 changes as a result of a change in the concentration of one medium such as water in another medium such as oil in a range, say of zero percent to two percent, the oscillator 30 will exhibit a frequency output signal as shown in FIG. 4. A curve 71 having discontinuities 72, 74, and 76, will be exhibited as the oscillator 30 is swept across its maximum frequency range, $f_1$ to $f_2$. Accordingly, as the oscillator is swept across its maximum frequency range indicated as $f_1$ to $f_2$ the number of discontinuities may be counted to determine what range of change in concentration of water in oil, for example, is being measured. For example, as shown in FIG. 5, a curve 73 having discontinuities indicated by the shifts 78, 80, 82, 84, 86, 88, and so on, would indicate that the oscillator 30 was measuring a change in frequency for a concentration of water in oil of say two percent to four percent. Therefore, the number of discontinuities measured per sweep of operating frequencies from $f_1$ to $f_2$ can indicate what range of variation in dielectric constant is being measured which correlates with the range of concentration of one medium such as water in the other medium such as oil.

Accordingly, by using an unisolated or unbuffered voltage controlled oscillator in a circuit such as described herein, an operating frequency at a particular control voltage may indicate the concentration of water in oil, for example, if after sweeping the oscillator across its frequency range, the number of 360° phase shifts counted are determined to determine the particular range of change of dielectric constant being experienced.

Figures 2, 6:
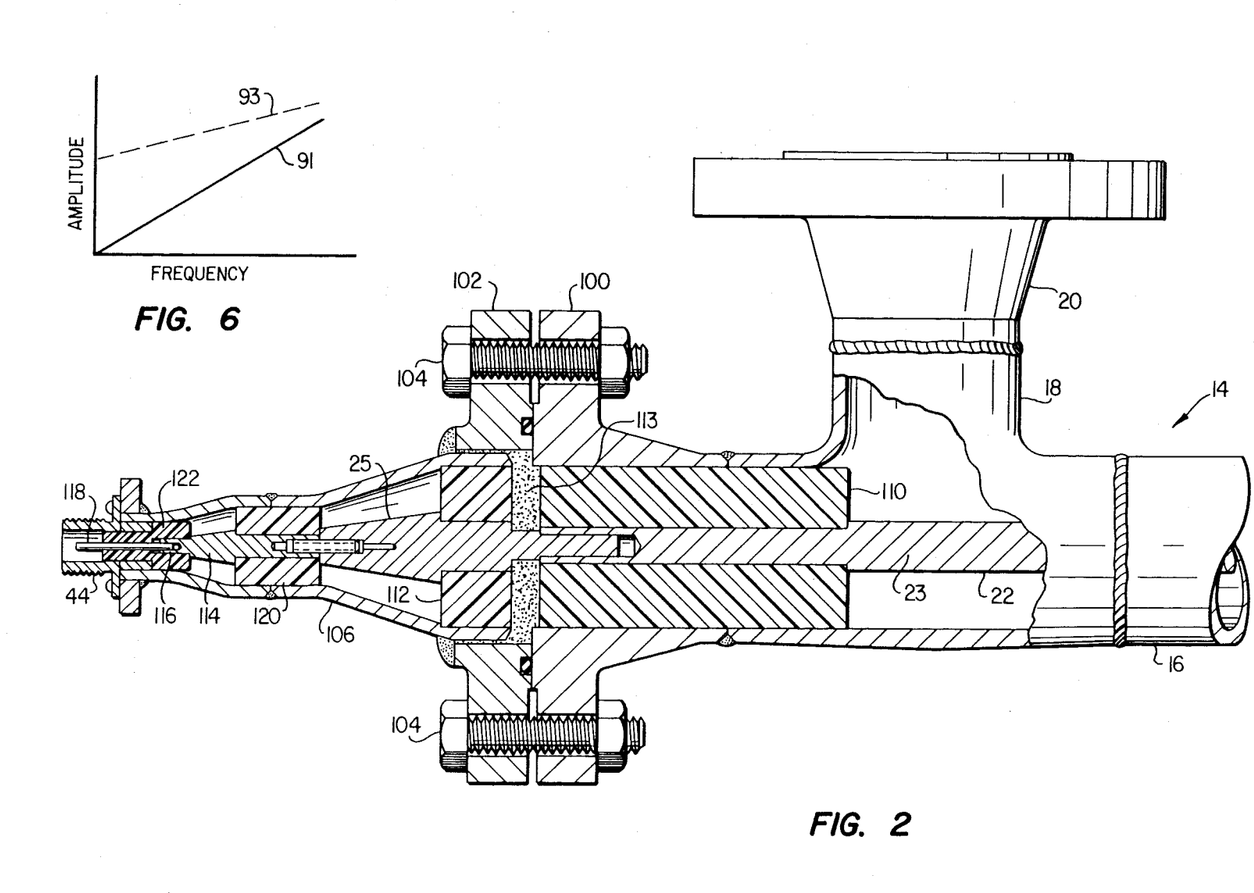
FIG. 2 is a section view of a portion of the combination coaxial waveguide or transmission line and fluid measurement section of the apparatus.
FIG. 6 is a diagram illustrating the effect of salinity of water in an oil-water mixture when measured by the apparatus of the present invention.

Referring now to FIG. 6, there is illustrated a diagram indicating the relationship between the oscillator signal frequency and amplitude and the effects of the salinity of a medium being measured, such as an oil-water mixture. The measurement of signal amplitude at several frequencies and a knowledge of the effect of salinity on the intercept of the frequency characteristic as a function of amplitude can correct for salinity effects on the overall impedance seen by the oscillator 30. For example, a salt-free fluid with a particular percentage of water in oil will exhibit a signal characteristic according to the curve 91 in FIG. 6 whereas the same percentage of water in a water-oil mixture with say, y moles percent of sodium chloride would exhibit a characteristic according to the curve 93 in FIG. 6.

Referring now to FIG. 2, there is illustrated a preferred arrangement of supporting the center conductor 22 within the measurement section 14 and terminating the center conductor at the conventional N type RF connector 44. The arrangement for terminating the conductor 22 at the end part 26 is essentially identical.

Each of the conduit "T"sections 18 is suitably welded to a conventional weldneck flange 100, as illustrated by way of example in FIG. 2, which in turn is secured to a flange 102 by conventional bolt and nut assemblies 104. The flange 102 is secured to a somewhat conical shaped reducer section 106. The internal space formed within the "T"section 18 and the weldneck flange 100 is occupied by a generally cylindrical block 110 formed of a suitable insulating material such as a flourocarbon plastic.

The center conductor 22 includes a generally cylindrical rod-like section 23 which is suitably supported in the block 110 and is in conductive relationship with a somewhat frustoconical conductor section 25 supported in a second support block 112 formed of an electrical insulating material. The conductor section 25 is secured to a third conductor section 114 by a conductive pin member 115. The conductor section 114 also has a somewhat frustoconical or tapered portion for reducing the diameter of the center conductor down to a portion 116 which is secured to a pin 118. The pin 118 comprises the center conductor for the connector 44. The conical tapered conductor sections 25 and 114 also prevent unwanted reflections of the signal being transmitted through the measurement section 14. Suitable insulating bushings or spacers 120 and 122 are adapted to support the conductor sections 25, 114, 116 and 118. A suitable insulating material and sealing, such as epoxy, may be injected to fill the cavity formed between the blocks 110 and 112, as indicated at 113, to prevent leakage of fluid from the interior of the conduit section 16 to the opposite ends of the measurement section 14. Thanks to the configuration of the end parts 24 and 26, there is little or no space provided which would create a void of non-flowing fluid within the measurement section 14 which might introduce errors into the determination of the concentration of one fluid in another being pumped through the measurement section. The "T"sections 18 might be replaced by conduit portions which would introduce flow into the conduit section 16 with a more gradual change of direction to minimize turbulence which could possibly effect the frequency readings being measured by the circuit described herein.

Although one preferred embodiment of the present invention has been described hereinabove, those skilled in the art will recognize that various substitutions and modifications may be made to the specific apparatus disclosed without departing from the scope and spirit of the appended claims.

What is claimed is:

1. Apparatus for measuring the concentration of one fluid such as water in another fluid such as oil using the alternate of microwave energy characteristics, said apparatus comprising:
   means forming a measurement section including a conduit for conducting a fluid mixture therethrough;
   microwave transmission means extending through said measurement section;
   an unisolated free running oscillator circuit operably connected to said transmission means for generating microwave energy for propagation through said measurement section at an operating frequency which changes with a change in the complex impedance of the oscillator load which includes the properties of said fluid mixture flowing through said measurement section;
   means for measuring a change in the operating frequency of said unisolated oscillator circuit resulting from the properties of the fluid mixture flowing through said measurement section; and
   means for comparing the change in frequency with a reference frequency corresponding to a certain concentration of one fluid in the other for determining the concentration of said one fluid in the fluid mixture flowing through said conduit.

2. The apparatus set forth in claim 1 wherein:
   said unisolated oscillator circuit includes a voltage controlled oscillator which may be controlled to sweep through a predetermined frequency range which is greater than the frequency range through which the oscillator may be pulled due to the changes in impedance caused by said fluid mixture, in said measurement section whereby the number of full phase shifts in the operating frequency range of said oscillator may be determined.

3. The apparatus set forth in claim 1 including:
   a second oscillator adapted to operate at a predetermined frequency;
   signal comparison means for comparing the operating frequency of said oscillators and for emitting a signal having a frequency which is related to the difference between the operating frequencies of said unisolated oscillator circuit and said second oscillator, and means for receiving the signal output from said comparison means.

4. The apparatus set forth in claim 1 wherein:
   said transmission means comprises a coaxial transmission line comprising a center conductor extending through said conduit and an outer conductor comprising said conduit.

5. Apparatus for measuring the concentration of one fluid such as water in another fluid such as oil using the alteration of microwave energy characteristics, said apparatus comprising:
   means forming a measurement section including a conduit for conducting a fluid mixture therethrough;
   a coaxial microwave transmission line extending through said measurement section comprising a center conductor extending through said conduit and having reduced diameter portions and an outer conductor comprising said conduit;
   said measurement section includes opposed end sections connected to said conduit and including means for supporting said reduced diameter portions of said center conductor;
   an unisolated oscillator circuit operably connected to said transmission means for generating microwave energy for propagation a through said measurement section at an operating frequency which changes with a change in the properties of said fluid mixture flowing through said measurement section;
   connector means connected to opposite ends of said reduced diameter portions of said center conductor for coupling said unisolated oscillator circuit to said measurement section;
   means for measuring a change in the operating frequency of said unisolated oscillator circuit resulting from the properties of the fluid mixture flowing through said measurement section; and
   means for comparing the change in frequency with a reference frequency corresponding to a certain concentration of one fluid in the other for determining the concentration of said one fluid in the fluid mixture flowing a through said conduit.

6. Apparatus for measuring the concentration of one fluid such as water in another fluid such as oil using the alteration of microwave energy characteristics, said apparatus comprising:

means forming a measurement section including a conduit for conducting a fluid mixture therethrough said conduit including inlet and outlet portions disposed at substantially opposite ends thereof for receiving and discharging a flow stream of said fluid mixture and said measurement section including means configured to minimize the stagnation of flow of said fluid mixture through said measurement section;

microwave transmission means extruding through said measurement section;

an unisolated oscillator circuit operably connected to said transmission means for generating microwave energy to propagation through said measurement section at an operating frequency which changes with a change in the properties of said fluid mixture flowing through said measurement section;

means for measuring a change in the operating frequency of said unisolated oscillator circuit resulting from the properties of the fluid mixture flowing through said measurement section; and means for comparing the change in frequency with a reference frequency corresponding to a certain concentration of one fluid in the other for determining the concentration of said one fluid in the fluid mixture flowing through said conduit.

7. Apparatus for measuring the concentration of one fluid such as water in another fluid such as oil using the alteration of microwave energy characteristics, said apparatus comprising:

means forming a measurement section including a conduit for conducting a fluid mixture therethrough;

microwave transmission means extending through said measurement section;

an oscillator circuit including a free running voltage controlled oscillator operably connected to said measurement section and adapted to be controlled to sweep through a predetermined operating frequency range which is greater than the frequency range through which the oscillator may be pulled due to the changes in impedance in said measurement section whereby the number of full phase shifts in the operating frequency range of said oscillator may be determined;

means for measuring a change in the operating frequency of said oscillator circuit resulting from a change in the complex impedance of the oscillator load which includes a change in the dielectric properties of the fluid flowing through said measurement section; and means for comparing the change in frequency with a reference frequency corresponding to a certain concentration of one fluid in the other for determining the concentration of one fluid in a fluid mixture flowing through said conduit.

8. The apparatus set forth in claim 7 including:
a second oscillator adapted to operate at a predetermined frequency;
signal comparison means for comparing the operating frequency of said oscillators and for emitting a signal having a frequency which is related to the difference between the operating frequencies of said oscillator circuit and said second oscillator, and means for receiving the signal output from said comparison means.

9. The apparatus set forth in claim 7 wherein:
said transmission means comprises a coaxial transmission line comprising a center conductor extending through said conduit and an outer conductor comprising said conduit.

10. The apparatus set forth in claim 7 including:
temperature sensing means including means for providing a signal to said comparison means to compensate for changes in temperature of said fluid as it affects said operating frequency.

11. Apparatus for measuring the concentration of one fluid such as water in another fluid such as oil using the alteration of microwave energy characteristics, said apparatus comprising:

means forming a measurement section including a conduit for conducting a fluid mixture therethrough;

means forming a coaxial microwave transmission line including an outer conductor comprising said conduit and a center conductor extending through said conduit;

an unisolated free running oscillator circuit operably connected to said transmission line for generating microwave energy for propagation through said measurement section at a frequency which changes with a change in the complex impedance of the oscillator load including the concentrations of the respective fluids in said fluid mixture;

a second oscillator adapted to operate at a predetermined frequency;

signal comparison means for comparing the operating frequency of said oscillators and for emitting a differential frequency signal which is related to the difference between the operating frequencies of said unisolated oscillator circuit and said second oscillator; and means for comparing said differential frequency signal with a reference frequency corresponding to a certain concentration of said one fluid in the fluid mixture flowing through said conduit.

12. Apparatus for measuring the complex impedance change of a radio frequency range signal commensurate with the composition of a medium of interest, said apparatus comprising:

means forming a measurement section and adapted to propagate said signal through said medium of interest;

an unisolated free running oscillator circuit having a fundamental operating frequency which changes as the complex impedance of the oscillator load changes and operably connected to said measurement section for generating radio frequency range energy for propagation through said measurement section;

means for measuring the operating frequency of said unisolated oscillator circuit resulting from the impedance characteristics of the circuit including said measurement section and said medium of interest; and means for comparing the measured frequency with a reference frequency corresponding to a complex impedance exhibited by a said measurement section including a particular composition of said medium of interest.

13. The apparatus set forth in claim 12 wherein:
said measurement section includes transmission means comprising a coaxial transmission line having a center conductor extending through a conduit and an outer conductor comprising said conduit, and said medium of interest is interposed in said measurement section between said conductors whereby the dielectric properties of said medium of interest affect the signal frequency and amplitude generated by said unisolated oscillator circuit.

14. The apparatus set forth in claim 13 wherein:
said unisolated oscillator circuit includes a voltage controlled oscillator which may be controlled to sweep through a predetermined frequency range which is greater than the frequency range through which the oscillator may be pulled due to the changes in impedance in said measurement secton whereby the number of full phase shifts in the operating frequency range of said unisolated oscillator circuit may be determined.

15. A method for measuring properties of a composition of matter using the alteration of microwave energy characteristics comprising the steps of:
providing apparatus including means forming a measurement section including means for transmitting microwave energy therethrough;
providing an unisolated free running oscillator circuit operably connected to said means for transmitting for generating microwave energy at an operating frequency which changes with a change in the complex impedance of the oscillator load which includes said properties of said composition of matter in said measurement section;
providing means for measuring a change in said operating frequency;
energizing said oscillator circuit and measuring changes in the operating frequency of said oscillator circuit due to changes in the composition of matter in said measurement section; and
comparing said changes in frequency with a reference frequency corresponding to a complex impedance exhibited by said measurement section including a particular composition of matter to determine said property of said composition of matter at the time of measuring said changes in frequency.

16. The method set forth in claim 15 including the step of:
operating said oscillator circuit to sweep through a predetermined frequency range greater than the frequency range which said oscillator circuit undergoes due to said changes in said properties to determine the number of full phase shifts in the operating frequency of said oscillator circuit.

17. The method set forth in claim 15 wherein:
said composition of matter comprises an oil-water mixture and said method includes the step of determining the salinity of said mixture by comparing microwave signal characteristics at selected measured frequencies of operation of said oscillator circuit with corresponding signal characteristics at the same measured frequencies for known salinity conditions of said fluid mixture.

* * * * *

UNITED STATES PATENT AND TRADEMARK OFFICE
CERTIFICATE OF CORRECTION

PATENT NO.   : 4,862,060
DATED        : Aug. 29, 1989
INVENTOR(S)  : Bentley N. Scott and Y. Sam Yang It is certified that error appears in the above-identified patent and that said Letters Patent is hereby corrected as shown below:

Column 7, line 54, delete "alternate" and insert --- alteration---.

Column 8, line 53, delete "a".

Column 9, line 16, delete "extruding" and insert --- extending ---.

Column 9, line 20, delete "to" and insert --- for ---.

Signed and Sealed this

Thirty-first Day of July, 1990

*Attest:*

HARRY F. MANBECK, JR.

*Attesting Officer*   *Commissioner of Patents and Trademarks*